United States Patent [19]

Conneely et al.

[11] Patent Number: 6,111,081
[45] Date of Patent: Aug. 29, 2000

[54] LACTOFERRIN VARIANTS AND USES THEREOF

[75] Inventors: Orla M. Conneely; Pauline P. Ward, both of Houston, Tex.

[73] Assignee: Baylor College of Medicine, Houston, Tex.

[21] Appl. No.: 08/866,544

[22] Filed: May 30, 1997

Related U.S. Application Data

[60] Provisional application No. 60/018,747, May 31, 1996.

[51] Int. Cl.[7] .......................... A61K 38/40; C07K 14/79; C12N 15/12; C12N 15/80
[52] U.S. Cl. .......................... 530/400; 530/350; 530/395; 435/69.1; 435/252.3; 435/254.11; 435/254.3; 435/320.1; 435/476; 435/477; 435/484; 536/23.5
[58] Field of Search ..................................... 530/350, 395, 530/400; 435/69.1, 252.3, 254.4, 254.3, 320.1, 476, 477, 484; 536/23.5

[56] References Cited

U.S. PATENT DOCUMENTS

| | | | |
|---|---|---|---|
| 4,016,100 | 4/1977 | Suzuki et al. | 252/316 |
| 4,289,690 | 9/1981 | Pestka et al. | 530/351 |
| 4,311,712 | 1/1982 | Evans et al. | 424/365 |
| 4,370,349 | 1/1983 | Evans et al. | 434/365 |
| 4,372,949 | 2/1983 | Kodama et al. | 424/199 |
| 4,394,443 | 7/1983 | Weissman et al. | 435/6 |
| 4,452,747 | 6/1984 | Gersonde et al. | 264/4.1 |
| 4,529,561 | 7/1985 | Hunt et al. | 264/4.3 |
| 4,634,665 | 1/1987 | Axel et al. | 435/68 |
| 4,652,639 | 3/1987 | Stabinsky | 536/27 |

(List continued on next page.)

FOREIGN PATENT DOCUMENTS

| | | |
|---|---|---|
| 0 206 783 A2 | 12/1986 | European Pat. Off. . |
| 0 556 699 A1 | 8/1993 | European Pat. Off. . |
| WO 87/00119 | 1/1987 | WIPO . |
| WO 89/01969 | 3/1989 | WIPO . |
| WO 91/05045 | 4/1991 | WIPO . |
| WO 91/13982 | 9/1991 | WIPO . |
| WO 92/04012 | 3/1992 | WIPO . |

OTHER PUBLICATIONS

Aisen, et al., "Iron Transport and Storage Proteins," *Ann. Rev. Biochem.* —49:357–393 (1980).

Alexander, et al. "Cloning and Sequencing of the Porcine Lactoferrin cDNA," *Animal Genetics*—23:251–256 (1992).

Alves, et al., "Monoclonal Antibodies to *Trypanosoma Cruzi* Inhibit Motility and Nucleic Acid Synthesis of Culture Forms," *Infect. Immun.*—39(1):377–382 (1983).

Ambruso, et al., "Lactoferrin Enhances Hydroxyl Radical Production by Human Neutrophils, Neutrophil Particulate Fractions, and an Enzymatic Generating System," *J. Clin. Invest.*—67:352–360 (1981).

Anderson, et al., "Struture of Human Lactoferrin at 3.2 A Resolution," *Proc. Natl. Acad. Sci. USA*—84:1769–1773 (1987).

(List continued on next page.)

*Primary Examiner*—Ponnathapura Achutamurthy
*Assistant Examiner*—William W. Moore
*Attorney, Agent, or Firm*—Albert P. Halluin; J. David Smith; Howrey & Simon

[57] ABSTRACT

The present invention is directed to recombinant nucleic acids encoding lactoferrin variants and portions thereof, having modified iron-binding capacity, and to vectors comprising same recombinant nucleic acids. The present invention is further directed to methods of producing such vectors, and to transfected cells harboring the same. Methods for the production of lactoferrin variants and portions thereof, in various eukaryotic or prokaryotic cells are also provided. Finally, the invention is directed to lactoferrin variants and portions thereof encoded by the nucleic acids of the invention and produced by the processes of the invention. Thus, the invention provides an efficient and economical means for the production of recombinant lactoferrin variants and portions thereof.

15 Claims, 4 Drawing Sheets

U.S. PATENT DOCUMENTS

| | | |
|---|---|---|
| 4,668,771 | 5/1987 | Kawakami et al. ............. 530/366 |
| 4,703,008 | 10/1987 | Lin ............................ 435/240.2 |
| 4,710,465 | 12/1987 | Weissman et al. ............. 435/91 |
| 4,725,442 | 2/1988 | Haynes ........................ 424/490 |
| 4,726,948 | 2/1988 | Prieels et al. ................ 424/94.4 |
| 4,737,323 | 4/1988 | Martin et al. ................. 264/4.3 |
| 4,740,461 | 4/1988 | Kaufman ...................... 435/68 |
| 4,766,075 | 8/1988 | Goeddel et al. .............. 435/240.2 |
| 4,800,159 | 1/1989 | Mullis et al. ................ 435/172.3 |
| 4,886,747 | 12/1989 | Derynck et al. ............... 435/69.4 |
| 4,920,016 | 4/1990 | Allen et al. .................. 424/450 |
| 4,921,706 | 5/1990 | Roberts et al. ................ 424/450 |
| 4,927,637 | 5/1990 | Morano et al. ................ 424/450 |
| 4,944,948 | 7/1990 | Uster et al. .................. 424/450 |
| 4,959,318 | 9/1990 | Foster et al. ................. 435/9.1 |
| 4,965,190 | 10/1990 | Woo et al. .................... 435/6 |
| 5,008,050 | 4/1991 | Cullis et al. ................ 264/4.3 |
| 5,009,956 | 4/1991 | Baumann ...................... 428/402.2 |
| 5,019,508 | 5/1991 | Johnson et al. ............... 435/198 |
| 5,081,227 | 1/1992 | Millan ........................ 530/328 |
| 5,155,037 | 10/1992 | Summers ....................... 435/240.2 |
| 5,304,633 | 4/1994 | Tomita et al. ................ 530/326 |
| 5,571,619 | 11/1996 | McAlphin et al. ............. 428/364 |
| 5,571,691 | 11/1996 | Conneely et al. ............. 435/69.1 |
| 5,571,697 | 11/1996 | Conneely et al. ............. 435/69.7 |
| 5,571,896 | 11/1996 | Conneely et al. ............. 530/400 |

OTHER PUBLICATIONS

Anderson, et al., Structure of Human Lactoferrin: Crystallographic Structure Analysis and Refinement at 28 A Resolution, *J. Mol. Biol.*—209(4):711–734 (1989).

Arnold, et al., "A Bactericidal Effect for Human Lactoferrin," *Science*—197:263–265 (1977).

Baker, et al., "New Prospectives on the Structure and Function of Transferrins," *J. Inorg. Biochem.* 47:147–160 (1992).

Bailey, et al., "Molecular Structure of Serum Transferrin at 3.3–A Resoultion," *Biochemistry*—27:5804–5812 (1988).

Bellamy, et al., "Antibacterial Spectrum of Lactoferrin B, a Potent Bactericidal Peptide Derived from the N–Terminal Region of Bovine Lactoferrin," *Journal of Applied Bacteriology*—73:472–479 (1992).

Bellamy, et al., "Identification of the Bacterial Domain of Lactoferrin," *Biochem. Biophys. Acta.*—1121:130–136 (1992).

Bluard–Deconinck, et al., "Iron Binding Fragments from the N–Terminal and C–Terminal Regions of Human Lactoferrin" *Biochem. J.*—171:321–327 (1977).

Broxmeyer, et al., "The Opposing Actions in Vivo on Maurine Myelopoiesis of Purified Preparations of Lactoferrin and the Colony Stimulating Factors," *Blood Cells*—13:31–48 (1987).

Broxmeyer, "Potential Therapeutic Usefulness of Lactoferrin in Leukemia," in *Nestle Research News* 1984/1985—p. 93 (1986).

Campbell, et al., "Isolation of a Lactoferrin cDNA Clone and its Expression in Human Breast Cancer," *British Journal of Cancer*—65(1):19–26 (1992).

Christensen, et al., "High Level Expression of Recombinant Genes in *Aspergillus Oryzae*," *Bio Technology*—6:1419–1422 (1988).

Crouch, et al., "Regulation of Cytokine Release From Mononuclear Cells by the Iron–Binding Protein Lactoferrin", *Blood*—80:235–240 (1992).

Cunningham, et al., "Structural Organization of the Mouse Lactoferrin Gene," *Biochemical and Biophysical Research Communications*—189(3):1725–1731 (1992).

Day, et al., "Structure of the Recombinant N–Terminal Lobe of Human Lactoferrin at 20 A Resolution," *J. Mol. Biol.*—232:1084–1100 (1993).

Day, et al., "Studies of the N–Terminal Half of Human Lactoferrin Produced from the Cloned cDNA Demonstrate That Interlobe Interactions Modulate Iron Release," *J. Biol. Chem.*—167(20):13857–13862 (1992).

Ellison, et al., "Damage of the Outer Membrane of Enteric Gram–Negative Bacteria by Lactoferrin and Transferrin," *Infect. Immun.*—56(11):2774–2781 (1988).

Epstein, et al., "Oral Candidiasis: Pathogenesis and Host Defense," *Review of Infectious Diseases*—6(1):96–106 (1984).

Fortkamp, et al., "Cloning and Expression in *Escherichia coli* of a Synthetic DNA for Hirudin, the Blood Coagulation Inhibitor in the Leech," DNA—5(6):511–517 (1986).

Fransson, et al., "Iron in Human Milk," *J. Pediatrics*—96(3):380–384 (1980).

Gatignol, et al., "Pheomycin Resistance Encoded by the ble Gene from Transposon Tn 5 as a Dominant Selectable Marker in *Saccharomyces Cerevisiae*," *Mol. Gen. Genet.*—207:342–348 (1987).

Gíslason, et al., "Receptor–Mediated Binding of Milk Lactoferrin to Nursing Piglet Enterocytes: A Model for Studies on Absorption of Lactoferrin–Bound Iron," *J. Pediatr. Gastroent. Nutr.*—21(1):37–43 (1995).

Gines, et al., "*Aspergillus Oryzae* has Two Nearly Identical Taka–Amylase Genes, Each Containing Eight Introns," *Gene*—79:107–117 (1989)./

Goodey, "The Production of Heterologous Plasma Proteins," *Tibtech*—11:430–433 (1993).

Goodman, et al., "Bovine Lactoferrin mRNA: Sequence, Analysis, and Expression in the Mammary Gland," *Biochemical and Biophysical Research Communications*—180 (1):75–84 (1991).

Hennart, et al., "Lysozyme, Lactoferrin, and Secretory Immunoglobulin A Content in Breast Milk: Influence of Duration of Lactation Nutrition Status, Prolactin Status, and Parity of Mother[1–3]," *Am. J. Clin. Nutr.*—53:32–39 (1991).

Hu, et al., "Lactoferrin Receptor of Mouse Small–Intestinal Brush Border," *Biochem. J.*—249:435–441 (1988).

Huge–Jensen, et al., "*Rhizomucor miehei* Triglyceride Lipase is Processed and Secreted from Transformed *Aspergillus Oryzae*," *Lipids* 24(9):781–785 (1989).

Hutchens, et al., "Structurally Intact (978–kDa) forms of Maternal Lactoferrin Purified from Urine of Preterm Infants Fed Human Milk: Identification of a Trypsin–Like Proteolytic Cleavage Event in vivo that does not Result in Fragment Dissociation," *Proceedings of the National Academy of Sciences, USA* 88:2994–2998 (1991).

Ish–Horowicz, et al., "Rapid and Efficient Cosmid Cloning," *Nucleic Acids Research I*—9(13):2989–2998 (1981).

Ito, et al., "Transformation of Intact Yeast Cells Treated with Alkali Cations," *J. Bacteriol.* 153(1):163–168 (1983).

Jeenes, et al., "A Truncated Glycoamylase Genes Fusion for Heterologous Protein Secretion from *Aspergillus Niger*," *FEMS Microbiology Letters* 107:267–272 (1993).

Jeltsch, et al., "The Complete Nucleotide Sequence of the Chicken Ovotransferrin mRNA," *Eur. J. Biochem.*—122:291–295 (1982).

Johnston, et al., "Correlation of Messenger RNA Levels with Protein Defects in Specific Granule Deficiency," *Blood*—80(8):2088–2091 (1992).

Kolotila, et al., "Stimulation of Neutrophil Actin Polymerization and Degranulation by Opsinized and Unopsinized *Candida albicans* Hyphae and Zymosan," *Infect. Immun.*—56(8):2016–2022 (1988).

Kunkel, et al., "Rapid and Efficient site–specific Mutagenesis without Pheotypic Selection," *Proc. Natl. Acad.* 82:488–492 (1985).

Laemmli, "Cleavage of Structural Proteins During the Assembly of the Head of Bacteriophage T4," *Nature*—227:680–685 (1970).

Lee, et al., "Generation of cDNA Probes Directed by Amino Acid Sequence: Cloning of Urate Oxidase," *Science*—239:1288–1291 (1988).

LeGrand, et al., "Characterization and Localization of an Iron–binding 18–kDa Glycopeptide Isolated from the N–Terminal Half of Human Lactotransferrin," *Biochimica et Biophysica Acta*—787(1):90–96 (1984).

Liang, et al., "Screening and Cloning a cDNA Coding for Lactoferrin from Human Mammary Gland," *J. Animal Sci.*—67:154 (1989).

Lineback–Zins, et al., "Preparation and Characterization of an $NH_2$–Terminal Fragment of Human Serum Transferrin Containing a Single Iron–Binding Site," *J. Biol. Chem.*—255(2):708–713 (1980).

Lönnerdal, et al., "Lactoferrin: Molecular Structure and Biological Function," *Annu. Rev. of Nutr.*—15:93–110 (1995).

Lydon, et al., "Nucleotide and Primary Amino Acid Sequence of Porcine Lactoferrin," *Biochimica et Biophysica Acta*—1132:97–99 (1992).

MacGillivray, et al., "The Primary Structure of Human Serum Transferrin," *J. Biol. Chem.*—258(6):3543–3553 (1983).

Machnicki, et al., "Lactoferrin Regulates the Release of Tumour Necrosis Factor Alpha and Interleukin 6 in vivo," *Int. J. Exp. Path.*—74:433–439 (1993).

Maniatis, et al., "The Isolation of Structural Genes form Libraries Eucaryotic DNA," *Cell*—15:687–701 (1978).

Masson, et al., "Lactoferrin in Milk from Different Species," *Comp. Biochem. Physiol.*—39:119–129 (1971).

Masson, et al., "Lactoferrin an Iron–Binding Protein Ni Neutrophilic Leukocytes," *J. Exp. Med.*—130:643–658 (1969).

Mazuier, et al., "Comparative Study of the Iron–Binding Properties of Human Transferrins," *Biochem. Biophys. Acta.*—629:399–408 (1980).

May, "The Highly Divergent Beta–Tubulins of *Aspergillus Nidulans* are Functionally Interchangeable," *J. Cell Biol.*—109:2267–2274 (1989).

McDonnell, et al., "High Level Expression of Biologically Active Estrogen Receptor in *Saccharomyces Cerevisiae*," *J. Steroid Biochem. Molec. Biol.*—39(3):291–297 (1991).

Mead, et al., "DNA and Protein Sequence of Bovine Lactoferrin," *Nucleic Acids Research*—18(23):7167 (1990).

Metz–Boutigue, et al., "Human Lactotransferrin: Amino Sequence and Structural Comparisons with Other Transferrins," *Eur. J. Bioch.*—145:659–676 (1984).

Mikogami, et al., "Apical–to–basolateral Transepithelial Transport of Human ILacoferrin in the intestinal Cell Line HT–29cl. 19A," *Am. J. Physiol.*—267:G308–G315 (1994).

Montreuil, et al., "Human Lactotransferrin: Structure and Function," in *Proteins of Iron Storage and Transport.* Spik et al., (Eds.) 25–38 (1985).

Mount, "A Catalogue of Splice of Junction Sequences," *Nucleic Acids Research*—10(2):459–472 (1982).

Nichols, et al., "Human Lactoferrin Stimulates Thymidine Incorporation into DNA of Rat Crypt Cells," *Pediatr. Res.*—21(6):563–567 (1987).

Osmani, et al., "Regulation of the mRNA Levels of nimA, A Gene Required for the G2–M Transition in *Aspergillus Nidulans*," *J. Cell Biol.*—104(23):1495–1504 (1987).

Panella, et al., "Polymorphism and Altered Methylation of the Lactoferrin Gene in Normal Leukocytes, Leukemic Cells, and Breast Cancer," —*Cancer Research* 51:3037–3043 (1991).

Pentecost, et al., "lactotransferrin is the Major Estrogen Inducible Protein of Mouse Uterine Secretions," *J. Biol. Chem.*—262(21):10134–10139 (1987).

Pierce, et al., "Molecular Cloning and Sequence Analysis of Bovine Lactotransferrin," *Eur. J. Bioch.*—196:177–184 (1991).

Powell, et al., "Nucleotide Sequence of Human Lactoferrin CdNA," *Nucleic Acids Research*—18(13):4013 (1990).

Rado, et al., "Isolation of Lactoferrin cDNA from a Human Myeloid Library and Expression of mRNA During Normal and Leukemic Myelopoiesis," *Blood*—70(4):989–993 (1987).

Rasmussen, et al., "Characterization and Expression of the Unique Calmodulin Gene of *Aspergillus Nidulans*," *J. Biol. Chem.*—265(23):13767–13775 (1990).

Reid "Molecular Cloning and characterization of the complementary DNA and gene coding for the B–chain of the subcomponent C1q of the human complement systen," Biochemical J.—231:729–735 (1985).

Rejman, et al., "Characterization of Lactoferrin Binding to the Mac–T Bovine Mammary Epithelial Cell Line Using a Biotin–Avidin Technique," *Int. J. Biochem.*—26(2):201–206 (1994).

Rey, et al., "Complete Nucleotide Sequence of Human Mammary Gland Lactoferrin," *Nucleic Acids Research*—18(17):5288 (1990).

Rose, et al., "Primary Stucture of the Human Melanoma–Assocaited Antigen p97 (Melanotransferrin) Duduced from the mRNA Sequence," *Proc. Natl. Acad. Sci. USA*—83:1261–1265 (1986).

Sawatzki, "The Role of iron Binding Proteins in Bacterial Infections" in *Iron Transport in Microbes, Plants and Animals* G. Winkelmann et al., (Eds.) 477–488 (1987).

Schaeffer, et al., "Complete Structure of the Human Tansferrin Gene. Comparison with Analogous Chicken Gene and Human Pseudogene," *Gene*—56:109–116 (1987).

Seyfert, et al., "Variants and Biotechnological use of the Bovine Lactoferrin–Encoding Gene," *Lacotferrin Interactions and Biological functions, Humana Press Inc., Totowa, NJ*—61–79 (1997).

Sheth, et al., "Cloning and Expression of the C–Terminal Lobe of Human Lactoferrin," *Advances in Experimental Medicine Biology*—357:259–263 (1994).

Shirsat, et al., "Structure of the murine lactoferrin gene is similar to the structure of other transferrin–encoding genes and shares a putative regulatory region with the murine myeloperoxidase gene," Gene 110:229–234 (1992).

Shively, et al., "Highlights of Protein Structural Analysis," *TIBS*—246–252 (1989).

Sofer, et al., "Designing an Optimal Chromatographic Purification Scheme for Proteins," *Biotechniques*—198–203 (1993).

Soukka et al., "Fungicidal Effect of Human Lactoferrin against *Candida allbicans*," *FEMS Microbiol. Lett.*—90–223–228 (1992).

Spik, et al., "Characterization and Properties of the Human and Bovine Lactoferrins Extracted from the Faeces of Newborn Infants," *Acta Paediatr Scand*—71:979–985 (1982).

Stowell, et al. "Expression of Cloned Human Lactoferrin in Baby–Hamster Kidney Cells," *Biochem. J.*—276:349–355 (1991).

Tabor, et al., "A Bacteriophage T7 RNA Polymerase/Promoter System for Controlled Exclusive Expression of Specific Genes," *Proc. Natl. Acad. Sci. USA*—82:1074–1078 (1985).

Teng, et al., "Assignment of the Lactotransferrin Gene to Human Chromosome 3 and to Mouse Chromosome 9," *Somatic Cell and Molecular Genetics*—(6):689–693 (1987).

Tenovuo, et al., "Antimicrobial Factors in Whole Saliva of Human Infants," *Infection and Immunity* 51(4):49–53 (1986).

Theil, et al., "The Storage and Transport of Iron in Animal Cells," in *Iron Transport in Microbes, Plants and Animals* G. Winkelmann et al., (Eds.) 491–520 (1987).

Towbin, et al., "Electrophoretic Transfer of Proteins from Polyacrylamide Gels to Nitrocellulose Sheets: Procedure and Some Applications," *Proc. Natl. Acad. Sci. USA*—76(9):4350–4354 (1979).

Tsang, et al., "Cloning of a 80–kD Advanced Glycosylation End Product (AGE) Binding Protein from Bovine Lung," *FASEB Journal*—Abstract No. 1431, (6):A233 (1991).

Tweedie, et al., "Lactoferrin cDNA," *Advances in Experimental Medicine Biology* 357:197–208 (1994).

Valenti, et al., "Interaction Between Lactoferrin and Ovotransferrin and Candida Cells," *FEMS Microbiology Letters*—33:271–275 (1986).

Vilja, et al., "A Rapid and Sensitive Non–Competitive Avidin–Biotin Assay for Lactoferrin," *J. Immunol. Meth.*—76:73–83 (1985).

Van Brunt, "Fungi: The Perfect Hosts?" *BioTechnology*—4:1057–1062 (1986).

von Heijne, "How Signal Sequences Maintain Cleavage Specificity," *J. Mol. Bio.*—173:243–251 (1984).

Ward, et al., "Improved Production of Chymosin In Aspergillus By Expression as a Glucoamylase–Chymosin Fusion,". *Bio/Technology*—8:435–440 (1990).

Ward, et al., "Production of Biologically Active Recombinant Human Lactoferrin in *Aspergillus Oryzae*," *Biotechnology*—10:784–789 (1992).

Ward, et al., "A System for Production of Commercial Quantities of Human Lactoferrin: A Broad Spectrum natural Antibiotic," *Biotechnology*—13:498–503 (1995).

Ward, et al., "An Inducible Expression System for the Production of Human Lactoferrin in *Aspergillus Nidulans*," *Gene*—122:219–223 (1992).

Waring et al., "Characterization of an Inducible Expression System in *Aspergillus Nidulans* Using alcA and Tubulin–Coding Genes," *Gene*—79:119–130 (1989).

Wei, et al., "Characterization of the Complete cDNA Sequence of Human Neutrophil Lactoferrin and Isolation of Genomic Cones," *Blood*—72(5):155a—Supplement 1—Abstract 531 (1988).

Wigler, et al., "Transformation of Mammalian Cells with Genes from Procaryotes and Eucaryotes," *Cell* 16:777–785 (1979).

Williams, et al., "The Evolution of Transferrin," *Trends in Biochem. Sci.*—7:394–397 (1982).

Wong, et al., "Human GN–CSF:Molecular Cloning of the Complementary DNA and Purification of the Natural and Recombinant Proteins," *Science*—810–815 (1985).

Wong, et al., "Reduced Glutathione Modulates $CA^{2+}$—Medicated Damage to Rabbit Isolated Gastric Mucosal Cells," *American Physiological Society*—G1–G9 (1994).

Yamauchi, et al., "Antibacterial Activity of Lactoferrin and a Pepsin Derived Lactoferrin peptide Fragment," *Infect. Immun.*—61(2):719–728 (1993).

Yang, et al., "Human Transferrin: cDNA Characterization and Chromosomal Localization," *Proc. Natl. Acad, USA*—81:2752–2756 (1984).

Yu, et al., "The Development Profile of Lactoferrin in Mouse Epididymis," *Biochem. J.*—296:107–111 (1993).

Zagulski, et al., "Lactoferrin Can Protect Mice Against a Lethal Dose of *Escherichia Coli* in Experimental Infection in vivo," *Br. J. Exp. Pathol.*—70:697–704 (1989).

FIG. 2A
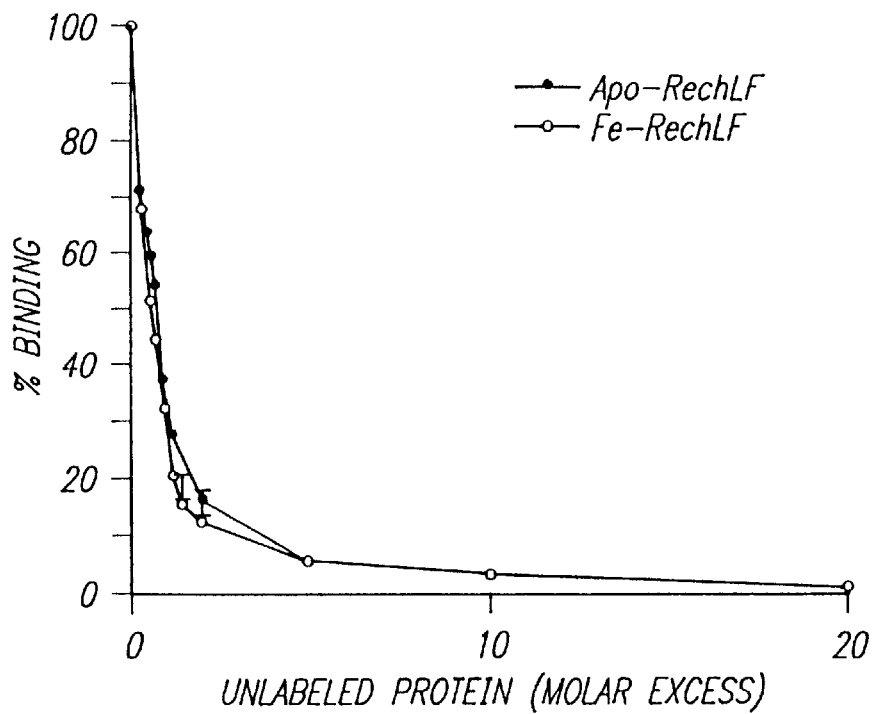
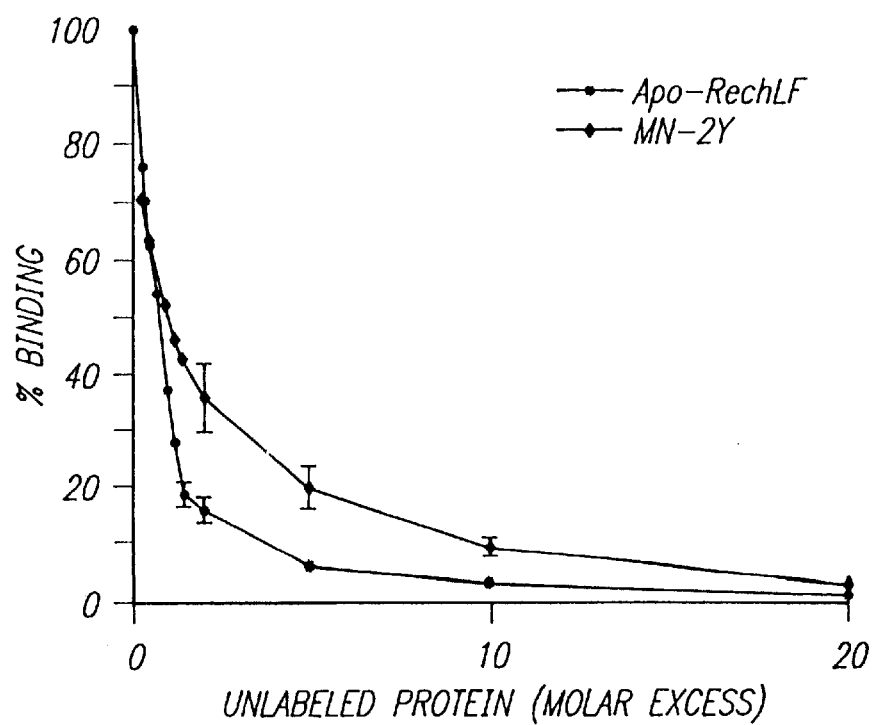
FIG. 2B

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

AGCGCGGCCG CAGGAGAAGG A                                               21

(2) INFORMATION FOR SEQ ID NO:2:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:2:

GATCCATGCG GCCGCATG                                                   18

(2) INFORMATION FOR SEQ ID NO:3:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:3:

AATTCATGCG GCCGCATG                                                   18

(2) INFORMATION FOR SEQ ID NO:4:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:4:

CACAGCCACG GCATAAGCGT GAGTTCGTGG CTG                                  33

(2) INFORMATION FOR SEQ ID NO:5:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

CTTGAAGGCA CCAGAGGCGC TGAAGTACGG TTC                                  33

(2) INFORMATION FOR SEQ ID NO:6:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

CACCGCCACA GCAAGGGCTC CTTCCACAGG TCT                                  33

```
(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CCGGAAAGCC CCAGTGGCGC CGTAGTATCT CTC                                    33
```

LACTOFERRIN VARIANTS AND USES THEREOF

The present application is a United States utility application based upon U.S. provisional application Ser. No. 60/018,747 filed on May 31, 1996.

I. FIELD OF THE INVENTION

The present invention generally relates to lactoferrin related glycoproteins. More specifically, the present invention relates to lactoferrin variants and portions thereof, their production and uses.

II. BACKGROUND OF THE INVENTION

Lactoferrin is a member of the transferrin family of non-heme iron binding glycoproteins (Aisen et al., 1980, *Ann. Rev. Biochem.* 49:357–393), which includes transferrin, the major iron-transport protein in blood (MacGillivray et al., 1983, *J. Biol. Chem.* 258:3543–3553), ovotransferrin, an avian egg white protein (Jeltsch et al., 1982, *Eur. J. Biochem.* 122:291–295) and melanotransferrin, a membrane bound form of this family found in human melanocytes (Rose et al., 1986, *Proc. Natl. Acad. Sci. USA* 83:1261–1265). Lactoferrin has a broad distribution, present in both external secretions that bathe the body surfaces (Masson et al., 1971, *Comp. Biochem. Physiol.* 39: 119–129; Hennart et al., 1991, *Am. J. Clin. Nutr.* 53:32–39; Masson et al., 1966, *Clin. Chim. Acta.* 14:735–739; Pentecost et al., 1987, *J. Biol. Chem.* 262:10134–10139; Yu et al., 1993, *Biochem. J.* 296:107–111) and in the secondary granules of polymorphonuclear neutrophils where it can be released into the bloodstream upon neutrophil activation (Masson et al., 1969, *J. Exp. Med.* 130:643–658). The functions proposed for lactoferrin include iron binding and delivery to the small intestine (Fransson et al., 1980, *J. Pediatrics* 96:380–384; Iyer et al., 1993, *Eur. J. Clin. Nutr.* 47:232–241; Cox et al., 1979, *Biochem. Biophys. Acta.* 558:129–141; Hu et al., 1988, *Biochem. J.* 249:435–441; Gislason et al., 1995, *J. Pediatr. Gastroent. Nutr.* 21:37–43; Mikogami et al., 1994, *Am. J. Physiol.* 267:G1–G8; Ward et al., 1995, *Biotechnology* 13:498–503), antimicrobial activity against a wide range of gram-negative and gram-positive bacteria (Oram et al., 1968 *Biochem. Biophys. Acta.* 170:351–365; Arnold et al., 1977, *Science* 197:263–265; Ellison et al., 1988, *Infect. Immun.* 56:2774–2781; Bellamy et al., 1992, *Biochem. Biophys. Acta.* 1221:130–136; Yamauchi et al., 1993, *Infect. Immun.* 61:719–728), cellular growth promotion (Hashizume et al., 1983, *Infect. Immun.* 763:377–382; Nichols et al. 1987, *Pediatr. Res.* 21:563–567), regulation of myelopoiesis (Sawatzki et al., 1989, *Blood Cells* 15:371–375; Broxmeyer et al., 1986, *Blood Cells* 13:31–48; Zucali et al., 1979, *Blood* 54:951–954), and immunomodulatory properties (Machnicki et al., 1993, *Int. J. Exp. Path.* 74:433–439; Crouch et al., 1992, *Blood* 80:235–240; Zagulski et al., 1989, *Br. J. Exp. Pathol.* 70:697–704).

Lactoferrin shares a high degree of structural homology with other members of the transferrin family. All of these proteins are monomeric glycoproteins with a molecular weight of ~80 kDa. Aisen et aL, 1980, *Ann. Rev. Biochem.* 49:357–393; Metz-Boutique et al., 1984, *Eur. J. Biochem.* 145:659–676. The three dimensional structure of lactoferrin (Anderson et al., 1989, *J. Mol. Biol.* 209:711–734) and transferrin (Lindley et al., 1988, *Biochem.* 27:5804–5812) have been precisely defined by X-ray crystallographic analysis. The proteins are folded into two globular lobes corresponding to the amino- and carboxy-terminal halves of the protein. This bilobal structure, with ~40% conservation between the amino- and carboxy-terminal halves, is thought have evolved by intragenic duplication from a common ancestral gene. Williams et al., 1982, *Trends Biochem. Sci.* 7:394–397. Each of these lobes can reversibly bind iron with high affinity and with the concomitant binding of an anion, usually carbonate. Aisen et al., 1980, *Ann. Rev. Biochem.* 49:357–393. The amino acids required for iron binding by lactoferrin are highly conserved between members of the transferrin family. Baker et al., 1992, *J. Inorg. Biochem.* 47:147–160. In lactoferrin, an iron atom binds to Asp 396, Tyr 93, Tyr 193 and His 254 in the amino-terminal lobe, and the corresponding Asp 396, Tyr 436, Tyr 539 and His 598 in the carboxy-terminal lobe, respectively. Anderson et al., 1989, *J. Mol. Biol.* 209:711–734.

Nonwithstanding their structural similarities, lactoferrin displays much more avid iron binding properties than its serum counterpart, transferrin. In particular, the release of iron from lactoferrin displays greater pH stability than transferrin, the latter releasing iron in a pH range of about six (6) to about four (4) while the former releases iron a pH range of about four (4) to about two (2). Mazuier et al., 1989, *Biochem. Biophys. Acta.* 629:399408. It has been suggested that the unique iron binding properties of lactoferrin contribute to some of the diverse functional activities proposed for this protein. Elucidation of the structural and functional features involved in the unique iron binding properties of lactoferrin will allow the modelling and generation of lactoferrin variants with improved properties, including, but not limited to, lactoferrin variants with higher affinity for iron for improved antimicrobial activities, lactoferrin variants with lower affinity for iron having improved iron releasing properties, or lactoferrin variants having modified pH dependent efficiencies for iron release.

The Applicants of the present invention have previously reported the high level production and characterization of recombinant human lactoferrin in the filamentous fungi, including Aspergillus. Ward et al., 1995, *Biotechnology* 13:498–503; U.S. Pat. Nos. 5,571,896, 5,571,619, and 5,571697, incorporated by reference in their entirety. Notwithstanding its distinct and unique carbohydrate composition, the recombinant protein was shown to be indistinguishable from human breast milk lactoferrin with respect to its physiological activities, including iron and receptor binding and antimicrobial activity. Hence, the availability of this expression system provides now the production of lactoferrin variants in sufficient quantities to address the structure/function role of this protein, in order to generate variants with improved properties.

III. SUMMARY OF THE INVENTION

The present invention relates to nucleic acid sequences encoding lactoferrin variants or portions thereof, wherein the portion comprises a sequence corresponding to at least one iron binding site of lactoferrin. The lactoferrin variant or portion thereof is further defined by having a modified iron binding capacity when compared to wild-type lactoferrin.

Using site-directed mutagenesis, the present invention elucidates the contribution of the two-lobe structure to the unique iron binding properties of lactoferrin. Human lactoferrin cDNA was selectively mutated in the two tyrosine residues involved in iron binding in either or both halves of the protein. The resulting three iron binding defective variants were expressed in and purified from *Aspergillus awamori*. Iron binding analysis using $^{59}FeCl_3$ confirmed that mutation of the two tyrosine residues involved in iron binding in either lobe, resulted in selective loss of iron binding to the mutated lobe. In addition, pH dependent iron-release studies demonstrated a differential iron binding stability of the two halves of lactoferrin, the amino-terminal lobe being much more acid-labile than the carboxy-terminal lobe. More importantly, the present invention shows that a functional iron binding carboxy-terminal lobe is necessary for the pH stability of iron binding to the amino-terminal lobe which is characteristic of wild-type lactoferrin. These results support the conclusion that cooperative interactions between the two lobes of lactoferrin contribute to the unique iron binding properties of this protein.

Thus, the present invention provides guidance for the generation of lactoferrin variants having improved properties, such as modified iron binding characteristics, e.g., increased or decreased affinity for iron, or modified pH or temperature requirements or ranges for iron binding. Furthermore, the present invention provides guidance for the modelling of lactoferrin variants having otherwise improved characteristics, e.g., therapeutic tolerance, while retaining their iron binding activity.

In a second aspect, the present invention is further directed to vectors comprising nucleic acids encoding lactoferrin variants or portions thereof, suitable for expression of the lactoferrin variant or portion thereof in eukaryotic cells. Preferably, the plasmid are suitable for expression in fungal cells, including *Aspergillus oryzae, Aspergillus niger, Aspergillus nidulans* and *Aspergillus awamori*.

In a third aspect, the present invention is further directed to methods of producing such vectors, and to transfected cells harboring the same. Methods for the production of lactoferrin and variants thereof in various eukaryotic or prokaryotic cells are also provided. Finally, the invention is directed to lactoferrins and variants thereof produced by the processes of the invention. Thus, the invention provides an efficient and economical means for the production of recombinant lactoferrin protein and variants thereof, and lactoferrin related polypeptides.

IV. BRIEF DESCRIPTION OF THE DRAWINGS

FIG. 1A depicts a Western immunoblot analysis of 200 ng samples of purified recombinant human lactoferrin (Rec hLF), amino-terminal (MN-2Y), carboxy-terminal (MC-2Y) and amino- and carboxy-terminal (MNC-4Y) iron binding defective variants of lactoferrin, respectively.

FIG. 1B depicts a Silver-stained SDS-polyacrylamide gel analysis of purified Rec hLF, MN-2Y, MC-2Y and MNC-4Y (1 μg each).

FIGS. 2A, 2B, 2C, and 2D depict competition of biotinlyated recombinant lactoferrin binding to human enterocyte cells by the iron binding defective lactoferrin variants.

FIG. 2A. Iron-saturated biotinylated recombinant human lactoferrin (0.4 μM) was incubated with Caco-2 membranes (300 ng) in the presence or absence of increasing concentrations of unlabeled iron-saturated recombinant lactoferrin (Fe-RechLF) or apo-recombinant lactoferrin (Apo-RechLF). Inhibition of biotinlyated lactoferrin binding to Caco-2 membranes was determined using a biotin/avidin microtiter assay (Ward et al., 1995, *Biotechnology* 13:498–503).

Figure 2C:
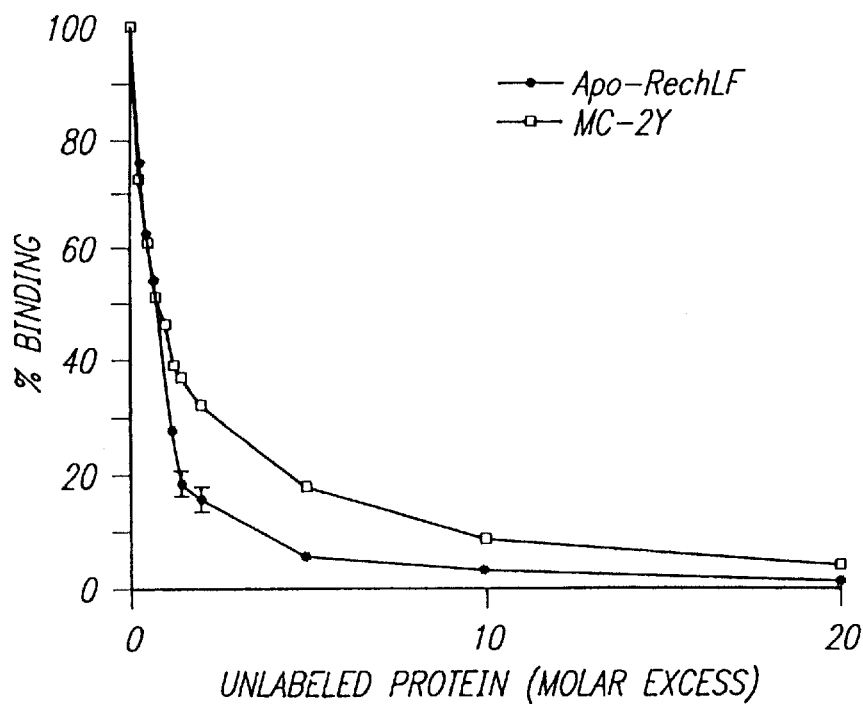
Figure 2D:
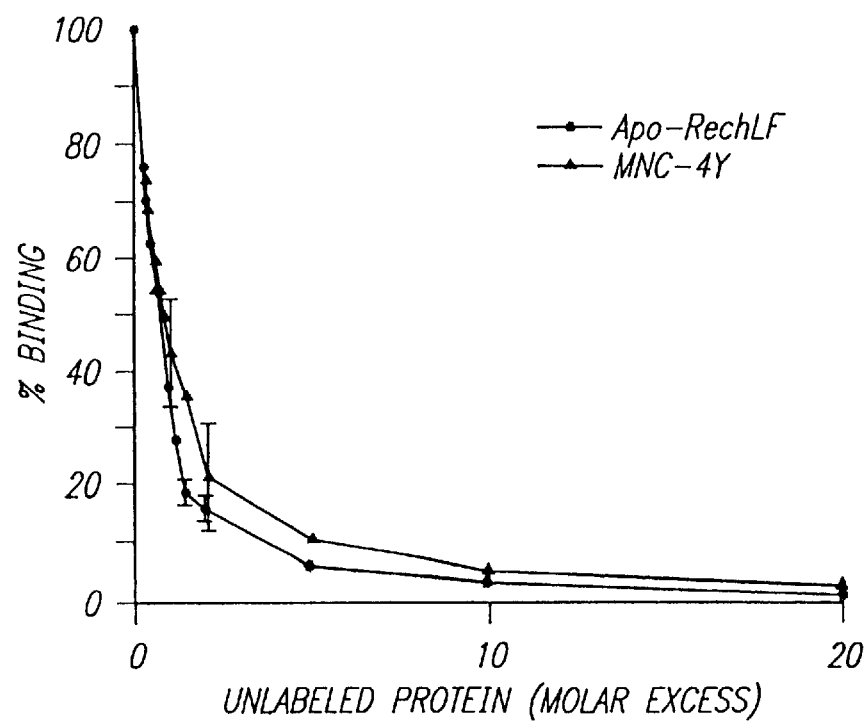

FIGS. 2B, 2C, and 2D. Apobiotinylated recombinant human lactoferrin (0.4 μM) was incubated with Caco-2 membranes (300 ng) in the presence or absence of increasing concentrations of unlabeled Apo-RechLF or MN-2Y (FIG. 2B), MC-2Y (FIG. 2C) or MNC-4Y (FIG. 2D). Inhibition of biotinylated lactoferrin binding to Caco-2 membranes was determined using a biotin/avidin microtiter assay. The data are represented as means ±S.E.M.

Figure 3:
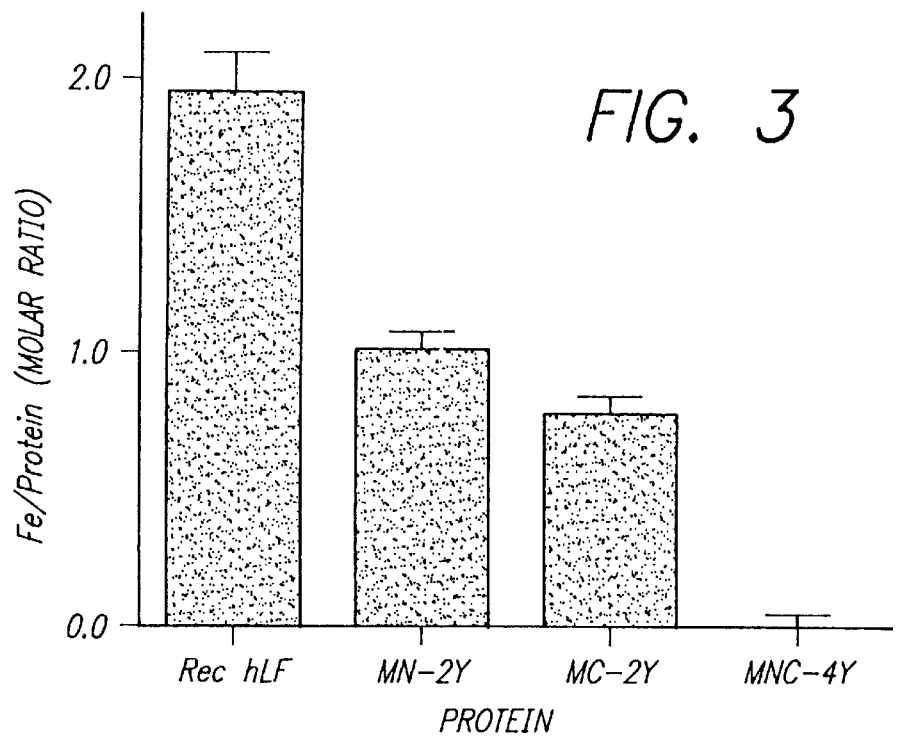

FIG. 3 depicts iron-saturation analysis of the lactoferrin amino-terminal (MN-2Y), carboxy-terminal (MC-2Y) and amino- and carboxy-terminal (MNC4Y) iron binding defective variants. Iron-free recombinant human lactoferrin (Rec hLF), MN-2Y, MC-2Y, and MNC-4Y were saturated with iron as described in the experimental procedures. $^{59}$Fe bound to the samples was quantified using liquid scintillation counting and the Fe/protein molar ratios were determined. The data are represented as means ±S.E.M.

Figure 4:
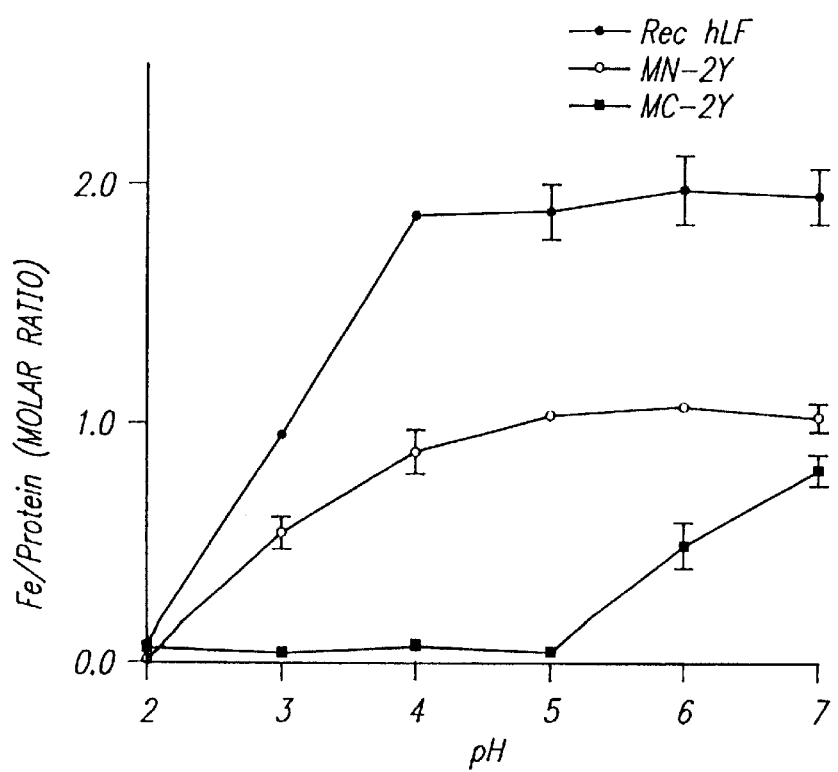

FIG. 4 depicts pH-dependent release of $^{59}$Fe from the lactoferrin amino-terminal (MN-2Y) and carboxy-terminal (MC-2Y) iron binding defective variants. $^{59}$Fe-saturated recombinant human lactoferrin (Rec hLF), MN-2Y and MC-2Y were dialyzed against buffers ranging in pH from 7–2. $^{59}$Fe remaining bound to the lactoferrin samples after dialysis was quantified by liquid scintillation counting and the Fe/protein molar ratio was determined. The data are represented as means ±S.E.M.

DEFINITIONS

Terms used herein are in general as typically used in the art. The following terms are intended to have the following general meanings as they are used herein:

The term "lactoferrin variant" refers to a polypeptide generated by mutation of a naturally occurring lactoferrin in at least one amino acid position.

The term "vector" means plasmid, cosmid, phage, virus, retrovirus or other vehicle to allow insertion, propagation and/or expression of a nucleic acid encoding a lactoferrin variant or portion thereof.

The term "host cell" means any cell that will allow lactoferrin expression.

The term "promotor" means regulatory DNA sequences that controls transcription of the lactoferrin cDNA.

The term "transformation" means incorporation permitting expression of heterologous nucleic acid sequences by a cell.

The term "iron binding capacity" means ability to bind Fe. Fully functional human lactoferrin can bind two atoms of iron per molecule of lactoferrin.

The term "biological activity/biological active" means biological activity of lactoferrin as measured by its ability to bind iron, or kill microorganisms, or retard the growth of microorganisms, or to function as an iron transfer protein.

VI. DETAILED DESCRIPTION OF THE INVENTION

A. Overview

The present invention is based, in part, on the identification those domains, sequences, and structures in the lactoferrin polypeptide which contribute to the iron binding capacity/properties of the protein. As such, the present invention provides guidance for the generation of lactoferrin variants having improved characteristics, such as modified iron binding characteristics, e.g., increased or decreased iron binding capacity, or modified pH or temperature requirements or ranges for the binding of iron. Furthermore, the present invention provides guidance for the modelling of lactoferrin variants having otherwise improved characteristics, e.g., therapeutic tolerance, stability against degradation, or immunoreactivity, while retaining their iron binding activity.

Accordingly, the present invention is directed to recombinant nucleic acids encoding lactoferrins variants and portions thereof, and to vectors comprising same recombinant nucleic acids. The present invention is further directed to methods of producing such vectors, and to transfected cells harboring the same. Methods for the production of lactoferrin variants and portions thereof in various eukaryotic or prokaryotic cells are also provided. Finally, the invention is directed to lactoferrins variants and portions thereof encoded by the nucleic acids of the invention and/or produced by the processes of the invention. Thus, the invention provides guidance for the design of lactoferrin variants or portions thereof having improved characteristics, and an efficient and economical means for the production of such lactoferrin variants and portions thereof.

B. Contribution of the Bilobal Structure of Lactoferrin to Its Unique Iron Binding Properties In the present invention, a site-directed mutagenesis approach was used to investigate the contribution of the bilobal structure of lactoferrin to the unique iron binding properties of this protein.

More specifically, the two tyrosines involved in iron binding in either or both lobes of lactoferrin were mutated to corresponding alanine residues in order to produce three iron binding defective variants. These lactoferrin variants were expressed and purified from *A. awamori* as previously described for the wild-type protein. U.S. Pat. No. 5,571,896; Ward et al., 1995, *Biotechnology* 13:498–503. The size, immunoreactivity and functional activity of these lactoferrin variants as determined by silverstain, western immunoblotting and enteric receptor binding analysis were similar to wild-type recombinant human lactoferrin indicating that the amino-acid substitutions had no adverse effect on the protein. Iron-saturation analysis using $^{59}FeCl_3$ showed that while the lactoferrin variant with an intact carboxy-terminal iron binding lobe saturate at the expected 1:1 ratio of iron to protein, the variant with an intact amino-terminal iron binding function consistently saturated at less than 1:1 suggesting a reduced stability of iron binding of this lactoferrin variant at pH 7.0. In addition, iron binding studies demonstrated that mutation of the tyrosine residues in both lobes effectively disrupted the iron binding capacity of the complete protein. See, Sections VII.A., VII.C., and VII.D.

As disclosed herein, pH dependent iron-release studies from the non-mutated lobes showed that the stability of iron binding to the amino- and carboxy-terminal lobes of lactoferrin were dissimilar. The release of iron from the lactoferrin variant containing an intact carboxy-terminal iron binding function was similar to that observed for the native lactoferrin. In contrast, the lactoferrin variant with an intact amino-terminal iron binding site was much more acid-labile, releasing all of its bound iron between a pH of 7–5. Hence, despite the overall structural homology between these two lobes (40%), it is demonstrated that the amino- and carboxy-terminal lobes of lactoferrin differ in their pH stability of iron binding. Furthermore, it is demonstrated that a functional iron binding carboxy-terminal lobe is required to impart the iron binding stability to the amino-terminal lobe which is characteristic of the wild-type protein.

The non-equivalence of iron binding to the amino and carboxy terminal lobes of lactoferrin has been reported previously. Mazuier et al., 1989, *Biochem. Biophys. Acta.* 629:399–408; Day et al., 1992, *J. Biol. Chem.* 167:13857–13862; Shimazaki et al., 1993, *J. Dairy Sci.* 76:946–955. Studies using a cloned amino-terminal fragment of human lactoferrin (Day et al., 1992, *J. Biol. Chem.* 167:13857–13862) and a proteolytically derived carboxy-terminal fragment from bovine lactoferrin (Shimazaki et al., 1993, *J. Dairy Sci.* 76:946–955) have shown a similar disparity in pH dependence of iron binding as reported in the present invention. However, while the previous reports did indicate that the carboxy-terminal lobe, or part thereof, was required to stabilize the amino-terminal lobe iron binding function, these studies were limited as it remained to be determined whether the structural presence of the carboxy-terminal lobe or a functional carboxy-terminal iron binding activity was required for stabilization of iron binding to the amino-terminal lobe. The present invention extends these studies and show that cooperative interactions, driven primarily by a functional carboxy-terminal lobe are necessary for iron binding stabilization.

The bias for selection of a bilobal structure in the evolution of the transferrin family is unknown. The instant disclosure provides a functional rationale for this selection in the case of lactoferrin. As such, the present invention shows that the evolution of a two lobe structure has endowed lactoferrin with unique iron binding properties which are likely to impinge on the unique functional activity of this protein. Interestingly, transferrin differs from lactoferrin in that it has been shown that the pH dependent iron release properties of this protein and a proteolytically derived amino-terminal fragment are similar. Mazuier et al., 1989, *Biochem. Biophys. Acta.* 629:399–408; Lineback-Zins et al., 1980, *J. Biol. Chem.* 255:708–713. These findings may suggest that a lack of cooperativity between the two lobes of transferrin may be a critical factor accounting for the characteristically weaker iron binding stability of this protein. Taken together with the studies described herein, it is suggested that the different iron binding properties of lactoferrin and transferrin may be due, at least in part, to the evolution of a carboxy terminal iron binding lobe of lactoferrin that has increased acid stability and functions cooperatively with the amino-terminal lobe to confer a pH stability to this lobe that is characteristic of the bilobal protein.

C. Lactoferrin Variants

Based on its identification of those domains, sequences and structures in the lactoferrin polypeptide contributing to the iron binding properties of the protein, the present invention provides guidance for the design and generation of novel lactoferrin variants or portions thereof having a modified iron binding capacity. Typically, the lactoferrin variants of the invention have improved properties, including, but not limited to, lactoferrin variants with higher affinity for iron for improved antimicrobial activities, lactoferrin variants with lower affinity for iron having improved iron-releasing properties, or lactoferrin variants having modified pH or temperature requirements or ranges for the binding and/or release of iron. In addition, the invention allows for the design of lactoferrin variants having otherwise improved characteristics, e.g., therapeutic tolerance, immunoreactivity, or biological half life, while retaining their iron binding capacity.

The lactoferrin variants of the invention may be derived from wild-type lactoferrin of a variety of mammalian species, including, but not limited to, human, murine, rat, bovine, and porcine lactoferrin. The wild-type lactoferrin may be mutated by a variety of methods generally known in the art. See, among other places, Sambrook et al., 1990, *Molecular Cloning: A Laboratory Manual.* Cold Spring Harbour Laboratory Press, New York; Kunkel et al., 1987, *Meth. Enzymol.* 154:367–382; Kunkel, 1985, *Proc. Natl. Acad. Sci. USA* 82:488–492.

In a preferred embodiment, the lactoferrin variant comprises at least one mutation affecting at least one iron binding site. Such iron binding site may have modified iron binding characteristics when compared to wild-type lactoferrin. For example, affinity for iron may increased or decreased. In addition, affinity for iron may exhibit modified pH range characteristics. Alternatively, the iron binding site may be modified such that the lactoferrin variant or portion thereof does not bind iron at all.

In another embodiment, the lactoferrin variant does comprise at least one mutation effecting modification of the therapeutic tolerance, biological stability or immunotolerance of lactoferrin, while retaining its biological activity.

D. Expression and Production of Lactoferrin Variants

The nucleic acid sequences of the invention encoding lactoferrin variants may be inserted in a vector suitable for its expression in a eukaryotic cell in such way that allows expression of the lactoferrin variant. Alternatively, nucleic acid sequences encoding portions of the lactoferrin variants of the invention may be inserted in vectors allowing their expression in eukaryotic cells. Preferably, the portion of the lactoferrin variant comprises at least one iron binding site, which may be modified.

In preferred embodiment, lactoferrin is produced in recombinant expression systems. See, among other places, Ward et al., 1992, *Biotechnology* 10:784–789; Ward et al., 1995, *Biotechnology* 13:498–503. For this purpose, nucleic acids coding for the desired form of lactoferrin (see, e.g., U.S. Pat. No. 5,571,691, incorporated by reference in its entity) is incorporated expressibly in a cellular host, which is then cultured under conditions appropriate for expression of that particular peptide or protein. A variety of gene expression systems have been adapted for this purpose, and typically drive expression of the desired gene from expression controls used naturally by the chosen host.

Because the lactoferrin variants of the invention typically, as natural occurring lactoferrin, requires post-translational modifications, such as glycosylation at several amino acid residues, many of the lactoferrins variants or portions thereof need to be produced in an eukaryotic host. In preferred embodiments, the lactoferrin product is produced by an Aspergillus expression system, as described in Ward et al., 1992, *Gene* 122:219–223; and U.S. Pat. Nos. 5,571,896 and 5,571,697, incorporated by reference in its entirety.

If unglycosylated forms of lactoferrin variants or portions thereof are produced, however, their production may conveniently be achieved in bacterial hosts such as *E. coli*. For such production, nucleic acid coding for the selected lactoferrin variant or portion thereof, may usefully be placed under an expression control, e.g., of the lac, trp or PL genes of *E. coli*.

As an alternative to expression of nucleic acid coding for the lactoferrin variant or portion thereof per se, the host can be adapted to express the lactoferrin product as a fusion protein in which the lactoferrin product is linked releasably to a carrier protein that facilitates isolation and stability of the expression product.

In a further alternative, the lactoferrin variant or portion thereof may be generated by organic synthesis. In particular where production of a portion of a lactoferrin variant, e.g., a peptide of about twenty (20) through about fifty (50) amino acids in length, is the objective preferably the well established techniques of automated peptide synthesis are employed, general descriptions of which appear, for example, in J. M. Stewart and J. D. Young, *Solid Phase Peptide Synthesis*, 2nd Edition, 1984, Pierce Chemical Company, Rockford, Ill.; and in M. Bodanszky and A. Bodanszky, *The Practice of Peptide Synthesis*, 1984, Springer-Verlag, New York; Applied Biosystems 430A Users Manual, 1987, ABI Inc., Foster City, Calif.; and *Solid Phase Peptide Synthesis—A Practical Approach*, by: E. Atherton & R. C. Sheppard, IRL Press, Oxford (1989). In these techniques, the lactoferrin variant portion is grown from its C-terminal, resin-conjugated residue by the sequential addition of appropriately protected amino acids, using either the Fmoc or tBoc protocols.

E. Applications

The lactoferrin variants of the present invention may be used for a broad variety of applications.

For example, a lactoferrin variant or portion thereof having improved iron binding capacity may be used for antimicrobial applications, including the treatment of infections, as additive to human or animal foods, as additive for eyedrops, eardrops, contact lense and other eye care solutions, topical skin care products, mouthwashes, chewing gum and toothpaste.

Lactoferrin variants or portions thereof having modified pH or temperature requirements may also be useful for the above applications. They further may be used as therapeutic additives for enhanced or modified iron transport and delivery.

Other applications of lactoferrin variants and portions thereof include the treatment of inflammatory skin diseases, as described in the co-pending provisional application, identified as Attorney Docket Number 8206–041–888, filed Apr. 10, 1997, hereby incorporated by reference in its entirety.

For many of the above identified applications, which are only to be understood as examples, lactoferrin variants and portions thereof having improved therapeutic tolerance, modified biological stability, or immunotolerance, may be particularly preferred.

F. Pharmaceutical Formulation and Routes of Administration

For therapeutic use, the lactoferrin variants or portions thereof chosen can be administered by any conventional means available for use in conjunction with pharmaceuticals, either as individual therapeutic agents or in a combination of therapeutic agents. Each can be administered alone but is generally administered with a pharmaceutical carrier selected on the basis of the chosen route of administration and standard pharmaceutical practice. The pharmaceutical compositions of the invention may be adapted for oral, parenteral, topical or rectal administration, or as inhalant, and may be in unit dosage form, in a manner well known to those skilled in the pharmaceutical art. Parenteral administration includes but is not limited to, injection subcutaneously, intravenously, intraperitoneally or intramuscularly.

Treatment with the active ingredient may begin at any time after the indication to be treated, e.g., infections, or skin disorders, e.g., psoriasis, contact dermatitis, UV-induced inflammation, infant diaper rash, asthma, arthritis, and the like, is diagnosed. Preferably, treatment is commenced as a prophylactic or at early stages of the disease, in order to prevent massive infection or inflammation in the first place. Typically, treatment will continue until the disorder is cured. In cases of chronic diseases, such as psoriasis, asthma or arthritis, or in cases of continued exposure to an allergen, the treatment may have to be extended beyond the cure of the symptoms.

The dose administered will, of course, vary depending upon known factors, such as (1) the pharmacodynamic characteristics of the particular lactoferrin product and its mode and route of administration, (2) the age, health, height and weight of the recipient, (3) the nature and extent of the symptoms, (4) the kind of concurrent treatment(s), (5) the frequency of treatment(s), and (6) the effect desired. A daily dose of active ingredient can be determined by those skilled in the art depending on the above factors.

The active ingredient may be administered topically, as inhalant, or as injection, e.g., in inflamed joints or cartilage. However, alternatively the lactoferrin variant may be administered orally in solid or semi-solid dosage forms, such as hard or soft-gelatin capsules, tablets, or powders, or in liquid dosage forms, such as elixirs, syrups, or suspensions. It can also be administered parenterally, in sterile liquid dosage forms. Other dosage forms are potentially possible such as patches or ointment or transdermal administration.

The lactoferrin variants of the invention may also be formulated as a slow release implantation device for extended and sustained administration of the lactoferrin product. Examples of such sustained release formulations include composites of biocompatible polymers, such as polyoactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical Sciences," M. Dekker, New York, 1990. Liposomes may also be used to provide for the sustained release of a lactoferrin variant or portion thereof. Details concerning how to use and make liposomal formulations of drugs of interest can be found in, among other places, U.S. Pat. No 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of a lactoferrin variant, e.g., in arthritic joints, or at local skin inflammations, etc.

Gelatin capsules or liquid-filled soft gelatin capsules may contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective disintegration in the gastrointestinal tract. Liquid dosage forms for oral administration can contain coloring and/or flavoring to increase patient acceptance.

Suitable pharmaceutical carriers are further described in *Remington's Pharmaceutical Sciences*, 17th ed., Mack Publishing Company, Easton, Pa. (1990) a standard reference text in this field, which is incorporated herein by reference in its entirety.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VII. EXAMPLES

A. Materials And Methods

Construction of pPLF-26, A Universal Aspergillus Awamori Expression Vector.

The construction of an expression vector, pPLF-19, for production of lactoferrin in *A. awamori* has previously been described. Ward et al., 1995, *Biotechnology* 13:498–503; U.S. Pat. No. 5,571,896. In order to construct an expression vector containing unique sites for cloning cDNAs encoding lactoferrin variants, pPLF-26 was generated. Briefly, pPLF-18 (Ward et al., 1995, *Biotechnology* 13:498–503) was digested with SphI generating two fragments of 3.3 kb and 4.4 kb. The 3.3 kb SphI fragment containing the lactoferrin cDNA was subcloned into SphI digested pALTER (Promega, Madison, Wis.) generating pLF18sp.Alt. The 4.4 kb SphI fragment was relegated generating PR18.2. In vitro mutagenesis using the commercially available pALTER kit (Promega, Madison, Wis.) was used to introduce a NotI restriction enzyme site at the start of mature lactoferrin cDNA in pLF18Sp.Alt generating pNot.9. The 5' phosphorylated oligonucleotide used for the mutagenesis was as follows: 5' AGCGCGGCCGCAGGAGAAGGA3' [SEQ ID NO: 1]. PR18.2 was digested with EcoRI and the resulting two fragments were repaired using the Klenow fragment of DNA polymerase I and religated in the correct orientation. The resulting plasmid, p▲E12, was digested with SphI and ligated with a 3.3 kb SphI fragment from pNot.9 generating pPLF-25. PL03, encoding the phleomycin resistance gene under the control of the β-tubulin promoter (Gatignol et al., 1987, *Mol. Gen. Genet.* 207:342–348) was digested with EcoRi and the resulting fragments were repaired using the Klenow fragment of DNA polymerase I and religated in the correct orientation. The resulting vector, PLO3▲R1, was digested with HindIII and the resulting 2.3 kb fragment was subcloned into HindIII digested pPLF-25 in the same orientation as the lactoferrin cDNA generating pPLF-26.

Constructing of Iron Binding Defective Variants of Lactoferrin, MN-2Y, MC-2Y and MNC4Y.

Synthetic 5' phosphorylated oligonucleotides with EcoRI/BamHI ends, were generated in order to introduce a NotI site into pALTER. The sequence of the oligonucleotides were as follows. Top strand 5'GATCCATGCGGCCGCATG 3' [SEQ ID NO:2]. Bottom strand: 5'AATTCATGCGGCCGCATG 3' [SEQ ID NO:3]. The oligonucleotides were annealed and ligated into EcoRI/BamHI digested pALTER generating pALTLink. pPLF-26 was digested with NotI/EcoRI and the resulting 2.1 kb fragment containing the human lactoferrin cDNA was subcloned into NotI/EcoRI digested pALTLINK. The resulting plasmid, pALThLF was used for subsequent mutagenesis experiments. The tyrosine residues involved in iron binding by lactoferrin in the amino-terminal lobe (Tyr 93, Tyr 193), carboxy-terminal lobe (Tyr 436, Tyr 529 and amino- and carboxy-terminal lobes (Tyr 93, Tyr 193, Tyr 436 and Tyr 529) were converted to corresponding alanine residues using in vitro mutagenesis using the pALTER kit. The 5' phosphorylated oligonucleotides used for the mutagenesis were as follows.

Tyr 93 → Ala 93: 5' CACAGCCACGGCATAAGCGTGAGTTCGTGGCTG 3'   [SEQ ID NO:4];

TYR 193 → Ala 193: 5' CTTGAAGGCACCAGAGGCGCTGAAGTACGGTTC 3'   [SEQ ID NO:5];

Tyr 436 → Ala 436: 5'CACCGCCACAGCAAGGGCTCCTTCCACAGGTCT 3'   [SEQ ID NO:6];

Tyr 529 → Ala 529: 5' CCGGAAAGCCCCAGTGGCGCCGTAGTATCTCTC 3'   [SEQ ID NO:7].

The resulting plasmids, pALTMN-2Y, pALTMC-2Y, and pALTMNC-4Y, were digested with NotI/EcoRI and subcloned into NotI/EcoRI digested pPLF-26 generating expression plasmids suitable for expression of lactoferrin in Aspergillus fungal cells, i.e., p26MN-2Y, p26MC-2Y and p26MNC-4Y, respectively. All oligonucleotides sequences and construction junction were sequenced using the commercially available Sequenase Version 2.0 kit (United States Biochemical Corporation, Cleveland Ohio).

Expression and Purification of MN-2Y, MC-2Y And MNC4Y.

The *A. awamori* expression vectors, p26MN-2Y, p26MC-2Y and p26MNC-4Y were transformed into *A. awamori* and transformants obtained were cultured for 7 days as previously described. Ward et al., 1995, *Biotechnology* 13:498–503. The culture medium was screened for the iron binding variants using an ELISA assay. Vilja et al., 1985, *J. Immunol. Meth.* 76:73–83. Positive cultures (>50 mg/l) were cultured in 2 liter flasks for 7 days and the lactoferrin variant wa purified using ion-exchange chromatography using CM-sephadex. Ward et al., 1995, *Biotechnology* 13:498–503. The proteins were dialyzed against 0.1 M citric acid followed by extensive dialysis against $H_2O$ and 5 mM sodium phosphate, pH 7.5 (3 g).

Receptor Binding Assays.

Receptor binding assays were performed using a biotin/avidin microliter plate assay (Rejman et al., 1994, *Int. J. Biochem.* 26:201–206) using 8 day old Caco-2 solubilized membranes (300 ng) essentially as described. Ward et al., 1995, *Biotechnology* 13:498–503.

Iron-Saturation and PH Stability of Iron Binding to the Lactoferrin Variants.

MN-2Y, MC-2Y and MNC-4Y (5 mg) were incubated with a four-fold excess of $FeCl_3$:$^{59}FeCl_3$:NTA (400:1:8). Ward et al., 1995, *Biotechnology* 13:498–503. The samples were incubated at room temperature for 30 minutes. The samples were purified through NAP-10 column (Pharmacia, Piscataway, N.J.) followed by dialysis against 0.05 M Tris/HCl, 0.2 M NaCl, pH 7.0 for 12 hours to remove any non-specific iron bound to the lactoferrin variants. Iron bound to the lactoferrin variants after dialysis was quantified by liquid scintillation counting. The pH stability of iron binding for each of the lactoferrin variants was carried out as described previously. Ward et al., 1995, *Biotechnology* 13:498–503.

B. Example 1

Expression and Purification of Iron Binding Defective Variants in the Amino and Carboxy-Terminal Domains of Lactoferrin In order to examine the contribution of the two-domain structure to the unique iron binding properties of lactoferrin, a site-directed mutagenesis approach was used to generate mutations in the human lactoferrin cDNA which encoded proteins which were defective in iron binding in either or both lobes of the protein.

Specifically, Tyr 93, Tyr 193 were mutated to Ala 93, Ala 193 generating a variant unable to bind iron in the amino-terminal half of lactoferrin (MN-2Y). The corresponding tyrosine residues in the carboxy-terminal half of lactoferrin Tyr 436, Tyr 529 were converted to alanine residues resulting in inactivation of the iron binding function of the carboxy-terminal domain (MC-2Y). All four tyrosine residues involved in iron binding by lactoferrin, i.e., Tyr 93, Tyr 193, Tyr 436 and Tyr 529, were also mutated to corresponding alanine residues generating a variant which was unable to bind iron in both lobes of lactoferrin (MNC-4Y).

Figure 1A:
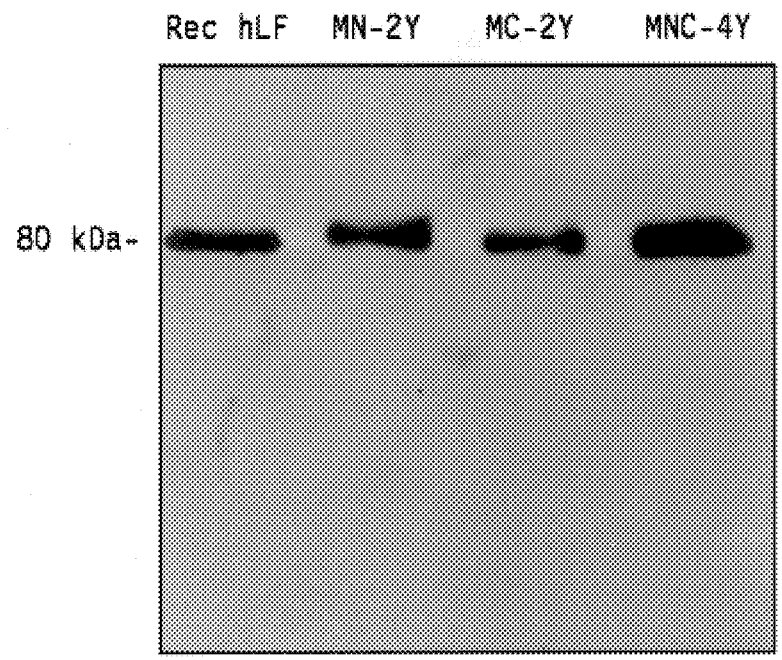
FIGS. 1A and 1B depict a Western immunoblot and silver stain analysis of the purified iron binding defective lactoferrin variants.
Figure 1B:
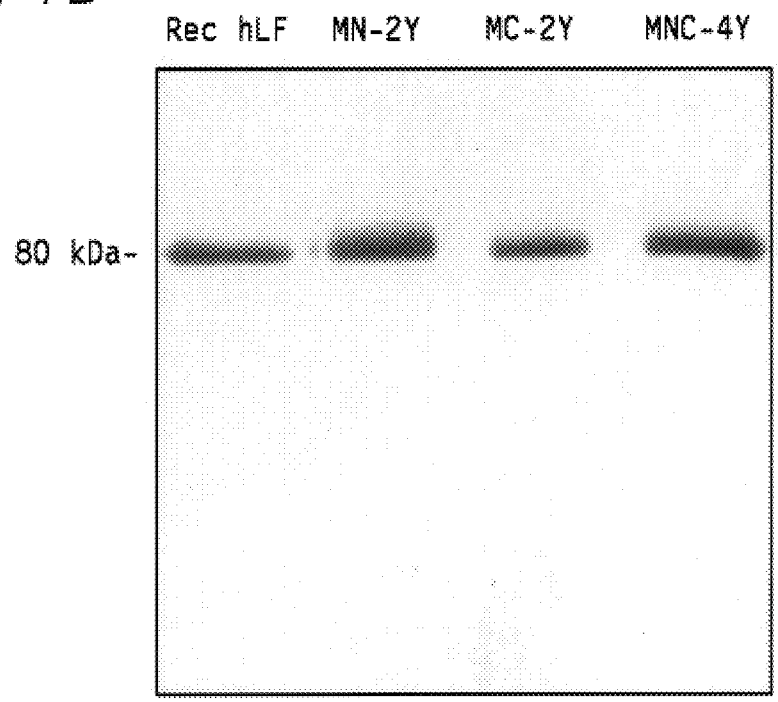

The lactoferrin variants were expressed and purified from *A. awamori* as previously described for recombinant human lactoferrin. Ward et al., 1995, *Biotechnology* 13:498–503, U.S. Pat. No. 5,571,896. The purified proteins were subjected to polyacrylamide gel electrophoresis followed by either western immunoblot analysis or silver stain analysis. See, FIG. 1. Western immunoblot analysis using a specific polyclonal IgG directed against human lactoferrin detected an immunoreactive band corresponding to the size of wild-type recombinant lactoferrin for each of the three lactoferrin variants, as depicted in FIG. 1A, lane 1–4. Analysis of a duplicate gel by silver stain analysis showed that the lactoferrin variants were >95 % pure and a single band at the expected molecular weight of ~80 kDa was observed for each of the proteins. See, FIG. 1B, lane 1–4. Hence, the size and immunoreactivity of the lactoferrin variants were indistinguishable from wild-type recombinant lactoferrin.

C. Example 2

The Iron Binding Defective Variants of Lactoferrin Have Similar Enteric Receptor Binding Properties to Wild-Type Recombinant Human Lactoferrin Based on the similarity of the amino acids alanine and tyrosine, it could be assumed that single amino-acid substitutions of tyrosine to alanine residues in the iron binding lactoferrin variant would result in minimal structural to the protein. Thus, the activity of the iron binding defective variants which are independent of iron binding, should be similar to that of wild-type recombinant human lactoferrin. Applicants and others have previously shown the presence of specific and saturable receptors for iron-saturated lactoferrin on human enterocyte cells. Iyer et al., 1993, *Eur. J. Clin. Nutr.* 47:232–241; Cox et al., 1979, *Biochem. Biophys. Acta.* 558:129–141; Hu et al., 1988, *Biochem. J.* 249:435–441; Gislason et al., 1995, *J. Pediatr. Gastroent. Nutr.* 21:37–43; Mikogami et al., 1994, *Am. J. Physiol.* 267:G1–G8; Ward et al., 1995, *Biotechnology* 13:498–503. Hence, as a prerequisite to using competitive receptor binding assay for the iron binding lactoferrin variants, the relative receptor binding kinetics of iron-free versus iron-saturated recombinant lactoferrin needed to be established.

Competitive receptor binding assays were performed as described previously. Ward et al., 1995, *Biotechnology* 13:498–503. Biotinylated iron-saturated recombinant human lactoferrin (0.4 $\mu$M) was incubated with human enteric Caco-2 cell membranes in the presence of O-20 fold molar excess of unlabelled apo- or iron-saturated recombinant human lactoferrin and a biotin/avidin microtiter assay was performed. Ward et al., 1995, *Biotechnology* 13:498–503. The results of this analysis are shown in FIG. 2A. Surprisingly, both apo- and iron-saturated lactoferrin showed comparable capacity to displace binding of iron-saturated biotinylated lactoferrin to the human enteric Caco-2 cell membranes indicating that both forms of lactoferrin have similar affinity for the lactoferrin enterocyte receptor. While lactoferrin has been proposed to deliver iron to enterocyte cells through these receptors, the similar relative receptor binding affinities or iron-free and iron-saturated lactoferrin suggest that the ability of lactoferrin to deliver iron via these receptors depends primarily on the relative amounts of iron-saturated versus iron-free lactoferrin present in the intestinal lumen.

Having established the affinity of apo-lactoferrin for its enteric receptor, competitive receptor binding assays with the lactoferrin variants were performed as described above to compare their functional activity with that of the wild-type protein. The results of this analysis are shown in FIGS. 2B, 2C, and 2D. All three iron binding defective variants showed no significant differences (<2-fold variation) in their capacity to specifically inhibit the binding of iron-free biotinylated lactoferrin to Caco-2 membranes as compared to wild-type protein. These results indicate that mutation of the tyrosine residues did not disturb the iron-independent receptor binding functional activity of the protein.

D. Example 3

Mutation of the Tyrosine Residues Involved in Iron Binding in the Amino- and Carboxy-Terminal Lobes of Lactoferrin Selectively Disrupts the Iron Binding Capacity of the Mutated Lobes of the Protein To confirm that mutation of the two tyrosine residues in either or both lobes of lactoferrin was sufficient to disrupt the iron binding ability of the mutated lobe, iron-saturation analysis using $^{59}FeCl_3$ was performed.

The results of this analysis are shown in FIG. 3. In the presence of a 4-fold excess of iron, the wild-type recombinant lactoferrin saturated at a 2:0 molar ratio of iron/protein as expected. While MN-2Y having an intact carboxy-terminal iron binding function was saturated at a 1:1 molar ratio, MC-2Y having an intact amino-terminus was saturated at less than 1:1 ratio indicating some possible iron loss from this lactoferrin variant at pH 7.0. Hence disruption of the tyrosine residues involved in iron binding in either the amino or carboxy terminal half o lactoferrin selectively abolished the iron binding ability of only the mutated lobe. In addition, the results from this analysis demonstrated that mutation of all four tyrosine residues involved in iron binding by lactoferrin effectively ablated the iron binding ability of this protein.

E. Example 4

Cooperativity Between the Amino- and Carboxy-Terminal Lobes of Lactoferrin Contribute to the Unique Iron Binding Stability of this Protein Having established that the iron binding defective lactoferrin variants were similar to wild-type recombinant lactoferrin, as determined by size, immunoreactivity and receptor-binding analysis, the pH-dependent iron release from these lactoferrin variants was analyzed to determine the contribution of the two-lobe structure to the iron binding stability of lactoferrin.

The lactoferrin variants were saturated with $^{59}FeCl_3$ and dialyzed against buffers ranging in pH from 7–2 for 48 hours at 4° C. The amount of iron remaining bound to the lactoferrin variants was quantified by liquid scintillation counting. The results of this analysis are shown in FIG. 4. The iron release profile from MN-2Y, containing an intact carboxy-terminal iron binding lobe, was similar to that of recombinant lactoferrin, iron release beginning at a pH of 5.0 and completed at pH 2.0. In contrast, the pH dependent release of iron from MC-2Y, containing an intact amino-terminal iron binding lobe, was markedly different. Release of iron from this variant began at a pH of 7.0, which is consistent with the lower than 1:1 iron saturation of MC-2Y (FIG. 4). In addition, iron release from MC-2Y was completed at a pH of 5.0. These results indicate that the amino-and carboxy-terminal lobes of lactoferrin differ in their pH stability of iron binding and a functional iron binding carboxy-terminal lobe is required to confer an increased pH stability to the amino-terminal domain that is characteristic of the wild-type protein. Based on these observations, it can be concluded that cooperative interactions between the two halves of lactoferrin, driven primarily by the carboxy-terminal lobe, contribute to the pH stability of iron binding that is unique to this protein.

All references cited within the body of the instant specification are hereby incorporated by reference in their entirety.

What is claimed:

1. A nucleic acid sequence encoding a lactoferrin variant or portion thereof, wherein said portion is further defined to comprise an amino acid sequence corresponding to at least one iron binding site of lactoferrin, and wherein the lactoferrin variant or portion thereof has a modified iron binding capacity, and wherein the amino acid sequence corresponding to at least one iron binding site of lactoferrin comprises a mutation or deletion of one or more amino acids selected from the group consisting of Asp 396, Tyr 93. Tyr 193 and His 254 in the amino-terminal lobe and Asp 396. Tyr 436. Tyr 529 and His 598 in the carboxy-terminal lobe.

2. A nucleic acid sequence encoding a lactoferrin variant selected from the group consisting of MN-2Y, MC-2Y and MNC-4Y.

3. A recombinant vector comprising:
   (a) a promoter;
   (b) DNA encoding the lactoferrin variant or portion thereof of claim 1; and
   (c) transcription and translation initiation and termination sequences;
wherein said vector is capable of producing the lactoferrin variant and expressing same as a processed protein.

4. A vector adapted for the expression of a lactoferrin variant or portion thereof in a eukaryotic cell, wherein said vector comprises DNA encoding a lactoferrin variant protein or portion thereof of claim 1 and regulatory elements necessary for the expression of said DNA in said cell.

5. A vector comprising:
   (a) a nucleic acid encoding the lactoferrin variant or portion thereof of claim 1; and
   (b) a promoter, and transcription and translation initiation and termination sequences;
wherein said vector is used for the expression of human lactoferrin in a eukaryotic cell.

6. A vector selected from the group consisting of p26MN-2Y, p26MC-2Y and p26MNC-4Y.

7. A transformed eukaryotic cell comprising the vector of claim 5.

8. The eukaryotic cell of claim 7, wherein said cell is selected from the group consisting of fungal, mammalian and insect cells.

9. The eukaryotic cell of claim 8, wherein said eukaryotic cell is a fungal cell selected from the group consisting of *Aspergillus oryzae, Aspergillus niger, Aspergillus nidulans* and *Aspergillus awamori.*

10. A transformed eukaryotic cell comprising a vector of claim 6.

11. The eukaryotic cell of claim 10, wherein said cell is selected from the group consisting of fungal, mammalian and insect cells.

12. The eukaryotic cell of claim 11, wherein said eukaryotic cell is a fungal cell selected from the group consisting of *Aspergillus oryzae, Aspergillus niger, Aspergillus nidulans* and *Aspergillus awamori.*

13. A method for producing the lactoferrin variant or portion thereof of claim 1 which comprises the following steps:
   (a) transforming a eukaryotic cell with a vector containing:
      i) the nucleic acid of claim 1; and
      ii) a promoter, and transcription and translation initiation and termination sequences;
   wherein said vector is adapted for the expression of the lactoferrin variant or portion thereof in a eukaryotic cell; and
   (b) culturing said transformed eukaryotic cell in a suitable nutrient medium until lactoferrin variant protein is formed, secreted into the nutrient medium, and isolated therefrom.

14. A lactoferrin variant or portion thereof encoded by the nucleic acid of claim 1.

15. A lactoferrin variant selected from the group consisting of MN-2Y, MC-2Y and MNC-4Y.

* * * * *